United States Patent
Basu et al.

(10) Patent No.: US 11,550,690 B1
(45) Date of Patent: Jan. 10, 2023

(54) PROVIDING RECOMMENDATIONS BASED ON MONITORED USER INPUTS

(71) Applicant: Adobe Inc., San Jose, CA (US)

(72) Inventors: Avirup Basu, New Delhi (IN); Apoorva, Noida (IN)

(73) Assignee: Adobe Inc., San Jose, CA (US)

( * ) Notice: Subject to any disclaimer, the term of this patent is extended or adjusted under 35 U.S.C. 154(b) by 0 days.

(21) Appl. No.: 17/517,966

(22) Filed: Nov. 3, 2021

(51) Int. Cl.
*G06F 3/0481* (2022.01)
*G06F 3/0484* (2022.01)
*G06F 11/34* (2006.01)

(52) U.S. Cl.
CPC ........ *G06F 11/3438* (2013.01); *G06F 3/0481* (2013.01); *G06F 3/0484* (2013.01)

(58) Field of Classification Search
CPC .. G06F 11/3438; G06F 3/0481; G06F 3/0484; G06F 11/3466
See application file for complete search history.

(56) References Cited

U.S. PATENT DOCUMENTS

| | | | |
|---|---|---|---|
| 2014/0371886 A1* | 12/2014 | Jain | G16H 20/30 700/91 |
| 2017/0083715 A1* | 3/2017 | Gupta | G06F 11/3024 |
| 2022/0091959 A1* | 3/2022 | Kripalani | G06F 3/0482 |

OTHER PUBLICATIONS

Enrique Costa-Montenegro et al., Which App? A Recommender System of Application in Markets by Monitoring Users' Interaction, Jan. 1, 2011, IEEE Xplore, pp. 353-354 (Year: 2011).*
Seokmin Lee et al., Interaction Data Analysis for Personalized Recommendation System, Nov. 1, 2020, IEEE Xplore, pp. 1-5 (Year: 2020).*
Xie, Y. et al., "Prevalence and risk factors associated with musculoskeletal complaints among users of mobile handheld devices: A systematic review," Applied ergonomics, 59(Pt A), Mar. 2017, pp. 132-142.

* cited by examiner

*Primary Examiner* — Tam T Tran
(74) *Attorney, Agent, or Firm* — NDWE LLP

(57) ABSTRACT

Embodiments are disclosed for providing workout recommendations based on monitored user inputs with a digital design system. In particular, in one or more embodiments, the disclosed systems and methods comprise receiving a series of inputs performed by a user with an application, categorizing each input in the series of inputs into a user interaction type, where each of the plurality of user interaction types is associated with a counter maintaining a detected user input count, determining that a first counter associated with a first user interaction type has exceeded a threshold amount, identifying a first action associated with the first user interaction type, and providing a notification message including information associated with the first action.

20 Claims, 15 Drawing Sheets

PROVIDING RECOMMENDATIONS BASED ON MONITORED USER INPUTS

BACKGROUND

Computing devices (e.g., computers, tablets, smart phones) provide numerous ways for users to capture, create, share, view, and otherwise edit numerous types of digital content, including images. However, many creative professionals are forced to terminate their careers prematurely due to various issues caused by their usage of computing devices, including incorrect posture and repetitive motions. In addition, tablets and mobile devices pose various ergonomic challenges when used for long durations.

Existing solutions can track the amount of time that a computing device is active. However, these existing solutions do not consider how the computing device is being used, and thus cannot provide recommendations to address potential negative impacts based on how the computing device is being used, resulting in imprecise recommendations.

These and other problems exist with regards to mitigating health issues related to computing device usage.

SUMMARY

Introduced here are techniques/technologies that allow a digital design system to generate notifications including a recommended action tailored for a specific user. To determine the user-specific action to recommend to a user, the digital design system monitors and tracks user interactions performed with the digital design system. The digital design system can also receive inputs from other applications on a user device indicating the type of user interactions performed with the other application. Using the user interaction data, the digital design system can identify how the user interactions may impact the health and well-being of the user, e.g., an impacted area of the user. For example, a series of small strokes for a long duration using a drawing application may be used by the digital design system to determine that a recommendation to perform a wrist exercise should be presented to the user. In other examples, long arcing strokes can strain a user's shoulder, using a mouse on a desktop application for a long time can stain a user's hand or fingers, and using a mobile device for an extended period of time can strain a user's eyes faster than a desktop or laptop, The digital design system can then identify an action (e.g., a workout, action, or exercise) that the user can perform to reduce or mitigate the negative impacts of the user's interactions on the health of the user. The digital design system can generate a notification message that is provided to the user that includes the information indicating the suggested or recommended actions for the user to perform. The digital design system can alter subsequent suggestions based on a response to the notification, where the response can indicate that the recommended should be skipped or dismissed as a future option.

Additional features and advantages of exemplary embodiments of the present disclosure will be set forth in the description which follows, and in part will be obvious from the description, or may be learned by the practice of such exemplary embodiments.

BRIEF DESCRIPTION OF THE DRAWINGS

The detailed description is described with reference to the accompanying drawings in which.

DETAILED DESCRIPTION

One or more embodiments include a digital design system configured to monitor user data indicating user interactions with the digital design system, or other applications, correlate the user interactions with potential user health issues, and generate recommendations or suggestions for mitigating the potential user health issues. The more a user performs interactions with a user device, the higher the likelihood that the user can develop health issue due to incorrect posture, repetitive motions, taking insufficient and/or inadequate breaks, and/or from lack of movement. Using user interaction data received by the digital design system, recommendations specific to the user and the user's interactions with the digital design system can be provided.

User data can include user device data indicating a type of user device (e.g., tablet, mobile device, laptop computer, desktop computer, etc.) being used by the user to interact with the digital design system. In addition, user data can include the types of user interactions being performed with the digital design system, including keystroke data, stylus data, touch screen interaction data, etc. While there are existing systems that track device usage, they have their disadvantages. For example, in such existing systems, device usage is based only on an amount of time.

In one existing solution, an operating system monitors the amount of time a user is using a particular user device and, after a predetermined amount of time, provides a notification to the user with a suggested action (e.g., take a break, go for a walk, etc.). In other existing solutions, an operating system may make assumptions about what the user is doing based on the amount of time the user device is in use. For example, if the user device is active for an hour, the operating system may assume the user has been looking at the screen for the entire hour and suggest the user take a break even if the user has not been actively interacting with the user device. These types of solutions are concerned only with the amount of time the user device is being used and do not consider the applications the user is interacting with and/or the types of interactions the user is performing with any applications on the user device. As a result, such systems are incapable of providing recommendations or suggestions based on any user-specific interaction data.

By determining recommendations for actions to be performed by a user based on the monitored user interaction data, embodiments of the present disclosure provide benefits and/or solve one or more of the foregoing or other problems in the existing systems.

Figure 1:
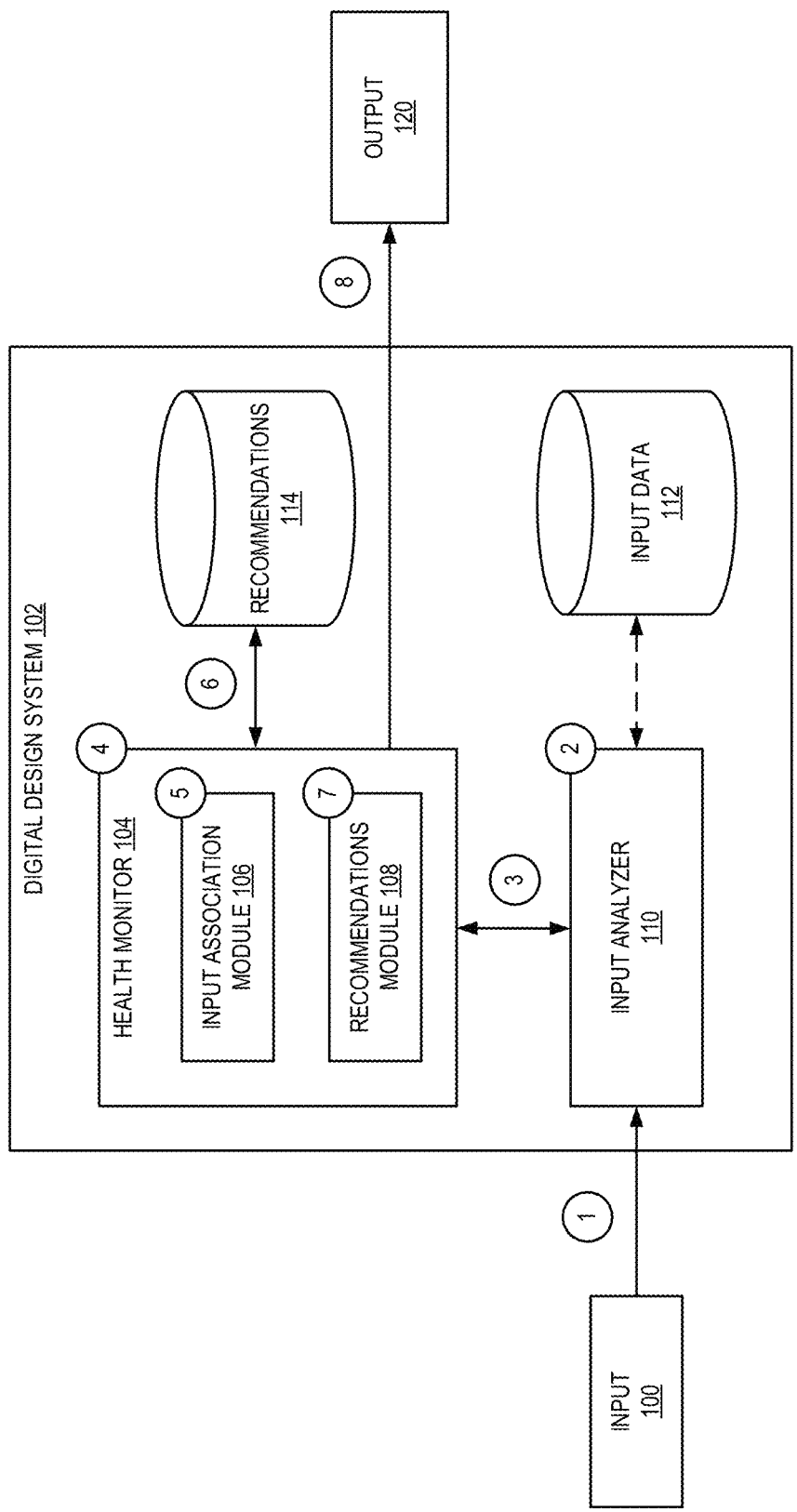
FIG. 1 illustrates a diagram of a process of providing recommendations based on monitored user interactions with a digital design system in accordance with one or more embodiments.

FIG. 1 illustrates a diagram of a process of providing recommendations based on monitored user interactions with a digital design system in accordance with one or more embodiments. As shown in FIG. 1, in one or more embodiments, a digital design system 102 receives an input 100, as shown at numeral 1. In one or more embodiments, the input 100 includes user interaction data associated with user interactions performed with the digital design system 102 and/or user interactions performed with another application and sent to the digital design system 102. In one or more embodiments, the digital design system 102 includes an input analyzer 110 that receives the input 100.

In one or more embodiments, the input analyzer 110 analyzes the input 100, as shown at numeral 2. In one or more embodiments, the input analyzer 110 analyzes the input 100 to identify user interaction data. The user interaction data can include keystroke data, stylus data, touch screen interaction data, etc. The user interaction data can include discrete user interactions (e.g., a user tap on a touch screen) and/or a series of user interactions performed over a period of time (e.g., a series of user strokes performed using one or more input devices).

The input 100 can also include a user identifier that identifies a user of the digital design system 102. The input 100 can also include user device data, including a device identifier, that can indicate a type of user device (e.g., tablet, mobile device, laptop computer, desktop computer, etc.) being used by the user to interact with the digital design system 102.

In one or more embodiments, after the input analyzer 110 analyzes the user interaction data, the user interaction data is sent to the health monitor 104, as shown at numeral 3. In one or more other embodiments, the input analyzer 110 optionally stores the input 100, including the user interaction data, in a memory or storage location (e.g., input data database 112) for later access by the health monitor 104. In one or more other embodiments, the user interaction data is also sent to a digital editor to perform the actions specified by the user interaction data.

At numeral 4, the health monitor 104 receives the input 100. In one or more embodiments, the health monitor 104 includes timer/counters. The health monitor 104 uses the timer to maintain a count of the amount of time that a particular user has been interacting with the digital design system 102 and/or other applications. The health monitor 104 uses the counters to maintain counts of user interactions, where each of a plurality of user interaction types is associated with a counter maintaining a detected user input count of the corresponding user interaction type.

In one or more embodiments, when the health monitor 104 begins receiving the input 100, including the user interaction data, the health monitor 104 determines whether to reset a timer and/or counters associated with a particular user in timers/counter. For example, when the health monitor 104 first begins receiving the user interaction data after a predefined threshold period of time without receiving user interaction data, the health monitor resets a timer and counters to zero, associated with a particular user identifier or device identifier, and begins monitoring the user interaction data of a particular user. In such embodiments, the health monitor 104 continues to monitor the usage time of the particular user until the health monitor 104 detects that the predefined threshold period of time has elapsed without receiving user interaction data. Assuming the threshold period of time has not elapsed, when the health monitor 104 receives user interaction data, the health monitor 104 does not reset the timer or the counters and continues the counts of user interaction types from their current value.

At numeral 5, an input association module 106 categorizes the user interaction data into one of a plurality of user interaction types. In such embodiments, input association module 106 increments counters corresponding to the user interaction type detected. For example, if the input association module 106 identifies that the user interaction data includes one or more long swipes performed by the user, the input association module 106 can increment a counter associated with a long stroke user interaction type. In another example, if the input association module 106 identifies one or more user interactions involving a mouse or stylus, the input association module 106 can increment a counter associated with a mouse inputs user interaction type.

In one or more embodiments, the health monitor 104 continues to receive user interaction data and continues to increment counters. When the timer reaches a predetermined time limit or a user interaction type counter reaches a limit, the recommendations module 108 accesses or queries a recommendations database 114 to retrieve workout and/or actions based on the user interaction data, as shown at numeral 6. The timer and each of the counters may be associated with one or more recommendations specific to the timer or the user interaction type. For example, when the timer reaches a time limit, the recommendation retrieved from the recommendations database 114 could be to refrain from looking at the user device for a period of time (e.g., 15 minutes) to reduce eye strain or mitigate back issues caused by prolong usage. In another example, when a short strokes user interaction counter limit is reached, the recommendation retrieved from the recommendations database 114 can be to perform wrist workout. In one or more embodiments, the recommendation to perform the wrist workout can be independent of whether the timer has reached a time limit.

When the health monitor 104 accesses or queries the recommendations database 114, recommended workouts and/or actions can then be returned to the health monitor 104 based on the query.

In one or more embodiments, after the recommended workout and/or actions are retrieved from the recommendations database 114, the recommendations module 108 generates notification including information associated with the workouts and/or actions. For example, the information associated with the workouts and/or actions can include a text, audio, and/or video explanation of the recommended workouts and/or actions.

At numeral 8, the digital design system 102 returns an output 120. In one or more embodiments, after the process described above in numerals 1-6, the output 120 is sent to the user or computing device that provided the input 100 to the digital design system 102. For example, after the process described above in numerals 1-6, a notification message including the recommendation determined by the health monitor 104 based on the input 100 can be displayed in a graphical user interface.

Figure 2:
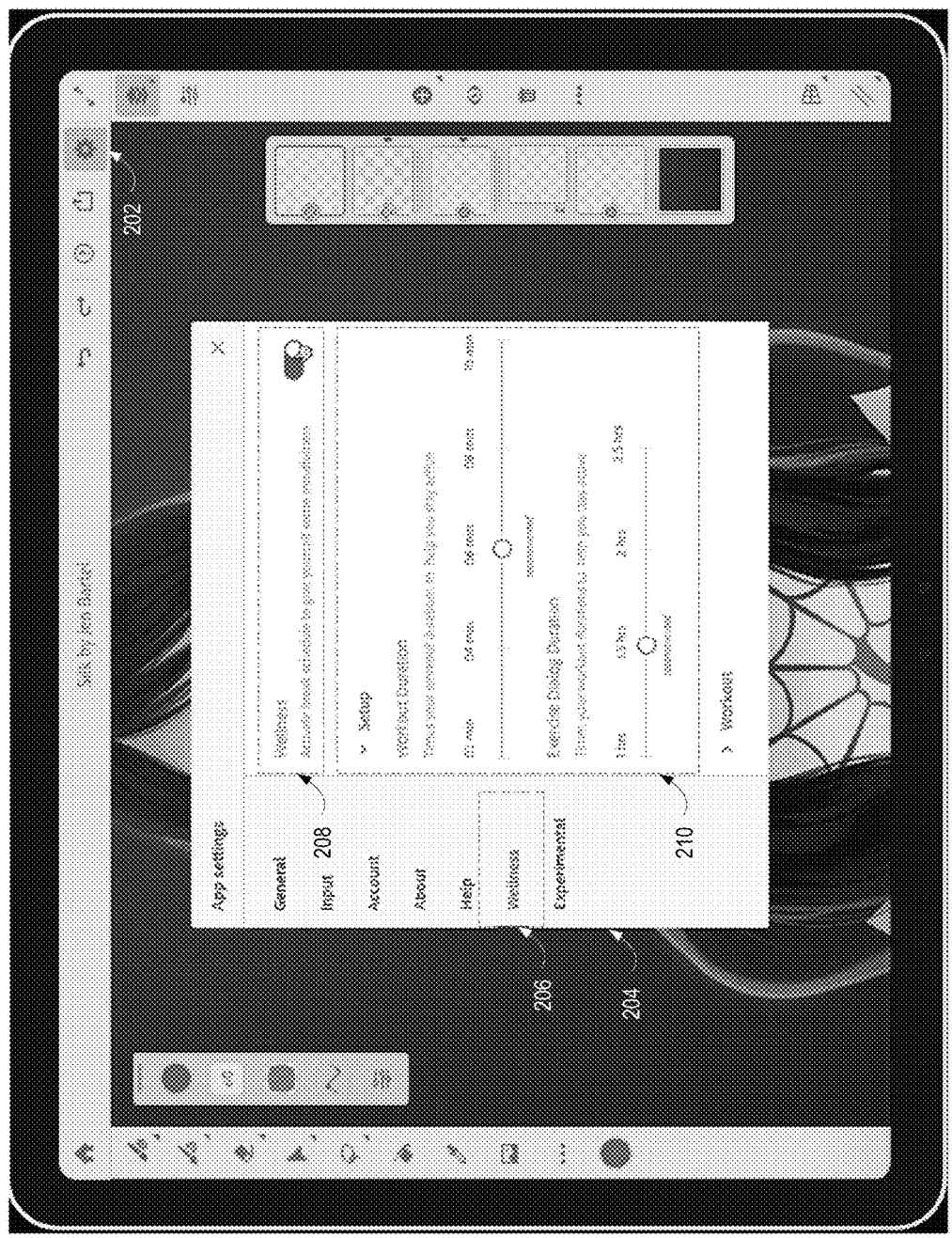
FIG. 2 illustrates an example health monitor settings interface of a digital design system in accordance with one or more embodiments.

FIG. 2 illustrates an example health monitor settings interface of a digital design system in accordance with one or more embodiments. As illustrated in FIG. 2, a digital design application is shown on a display of a user device 200. Upon selection of a settings interface element 202, an application settings interface 204 is displayed on the user device 200. The application settings interface 204 can include a plurality of options, including a wellness section. In response to selection of the wellness section interface element 206, a plurality of wellness section can be displayed. The overview section 208 includes an interface element to toggle the health monitor functionality on or off. In one or more embodiments, the setup section 210 includes user selectable options for workout duration and exercise dialog duration. The setup section 210 can display recommended values for duration and frequency of breaks. The workout duration option allows a user to set a duration of workouts or actions that will be recommended, where the user can adjust the duration to less than or greater than a recommended setting. The exercise dialog duration option allows a user to set the amount of time that passes between suggested breaks.

Figure 3:
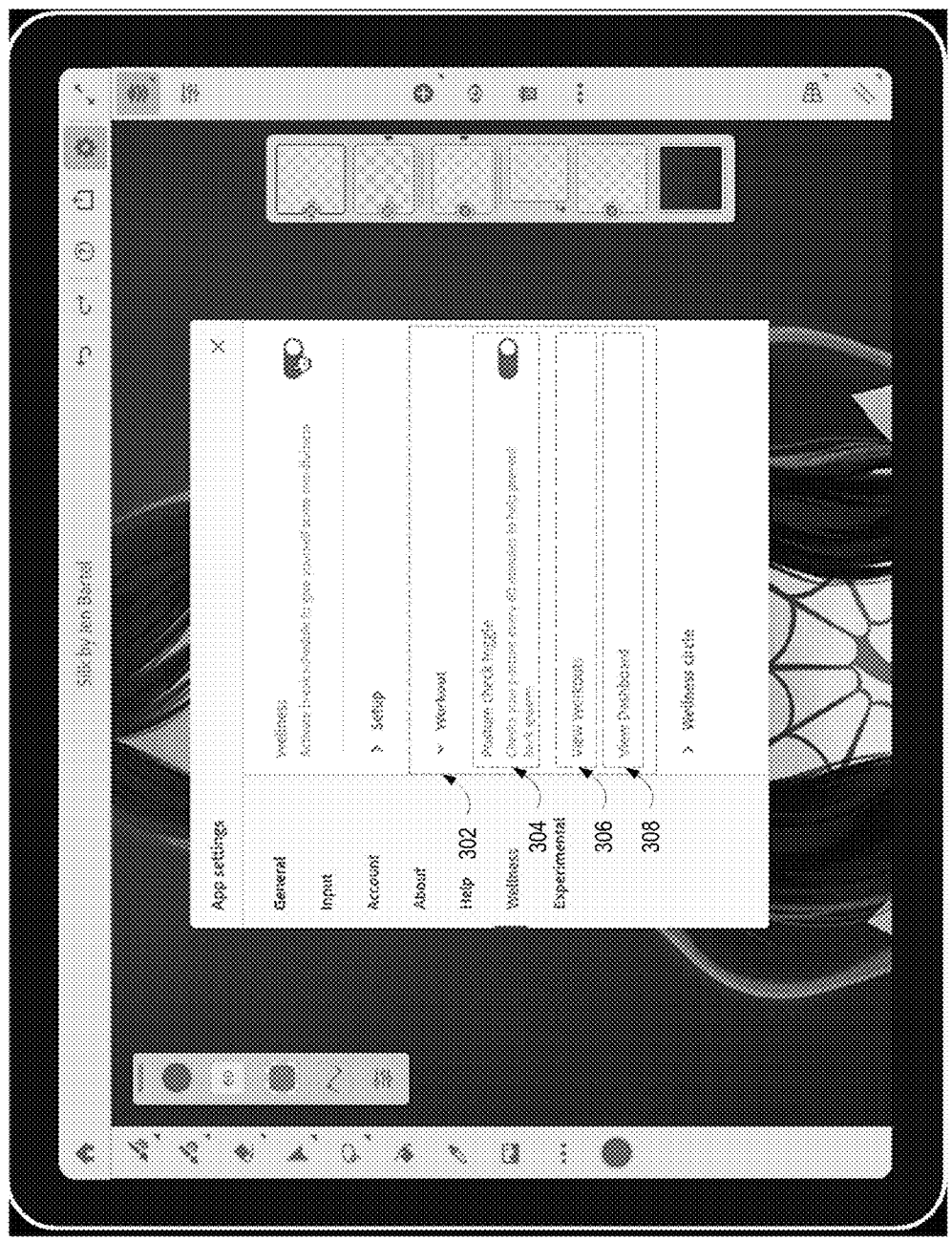
FIG. 3 illustrates an example health monitor settings interface of a digital design system in accordance with one or more embodiments.

FIG. 3 illustrates an example health monitor settings interface of a digital design system in accordance with one or more embodiments. As illustrated in FIG. 3, the wellness section can further include a workout section 302. In one or more embodiments, the workout section 302 includes a posture check interface element 304 that allows the user to enable or disable a posture checking functionality that periodically (e.g., every hour) provides a notification to the user to check their posture to mitigate injury or wellness issues caused by poor posture.

Figure 4:
FIG. 4 illustrates an example workouts interface of a digital design system in accordance with one or more embodiments.

The workout section 302 can also include an interface element 306 to allow a user to view workouts and an interface element 308 to allow a user to view a dashboard. FIG. 4 illustrates an example workouts interface of a digital design system in accordance with one or more embodiments. In response to selection of the interface element 306 in FIG. 3, a workouts interface 400 can be displayed on the user device 200. The workouts interface 400 can display favorite workouts, most repeated workouts, most recent workouts, etc. Each of the workouts can display workout-specific information, including duration of a video demonstration or explanation and the area of the body targeted for the workout. The workouts interface 400 can further include a filter 402 that allows a user to filter the list of displayed workouts by the duration of the workout and/or the workout area. The workouts interface 400 allows a user to favorite, or unfavorite, particular workouts/actions by selecting or deselecting an interface element (e.g., star icons 404A and 404B.

Figure 5:
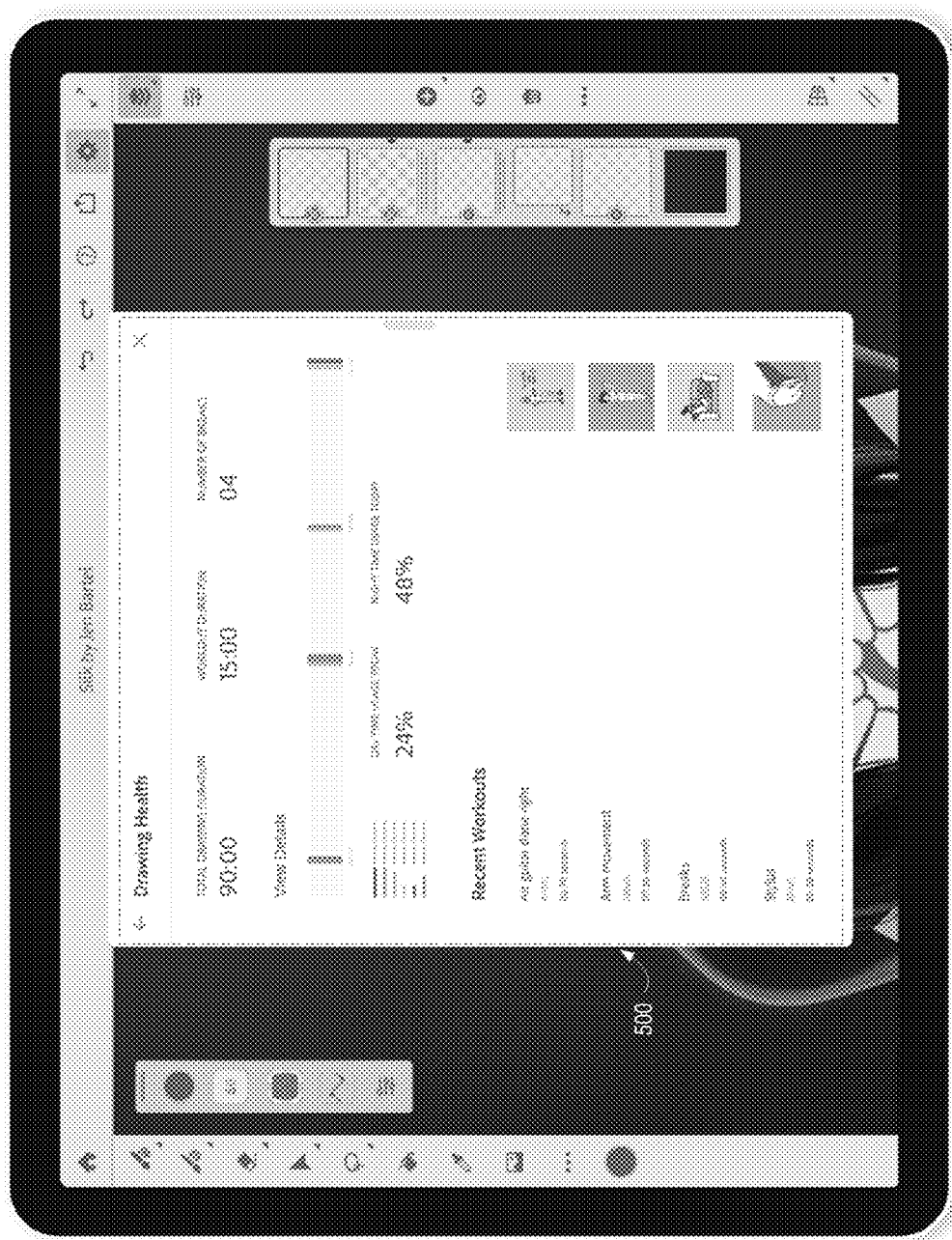
FIG. 5 illustrates an example health dashboard of a digital design system in accordance with one or more embodiments.

FIG. 5 illustrates an example health dashboard of a digital design system in accordance with one or more embodiments. In response to selection of the interface element 308 in FIG. 3, a dashboard interface 500 can be displayed on the user device 200. The dashboard interface 500 can display statistics about a user's interactions with the user device and/or the digital design system and aggregated information regarding workouts and actions that the user has indicated they have performed. The dashboard interface 500 can include timers indicating the total time the user has been interacting with the digital design application and the amount of time the user has indicated they have spent performing workouts. The dashboard interface 500 can also include information indicating the number of breaks taken by the user. The dashboard interface 500 can also include information (e.g., a listing) regarding recent workouts the user has indicated they have performed.

Figure 6:
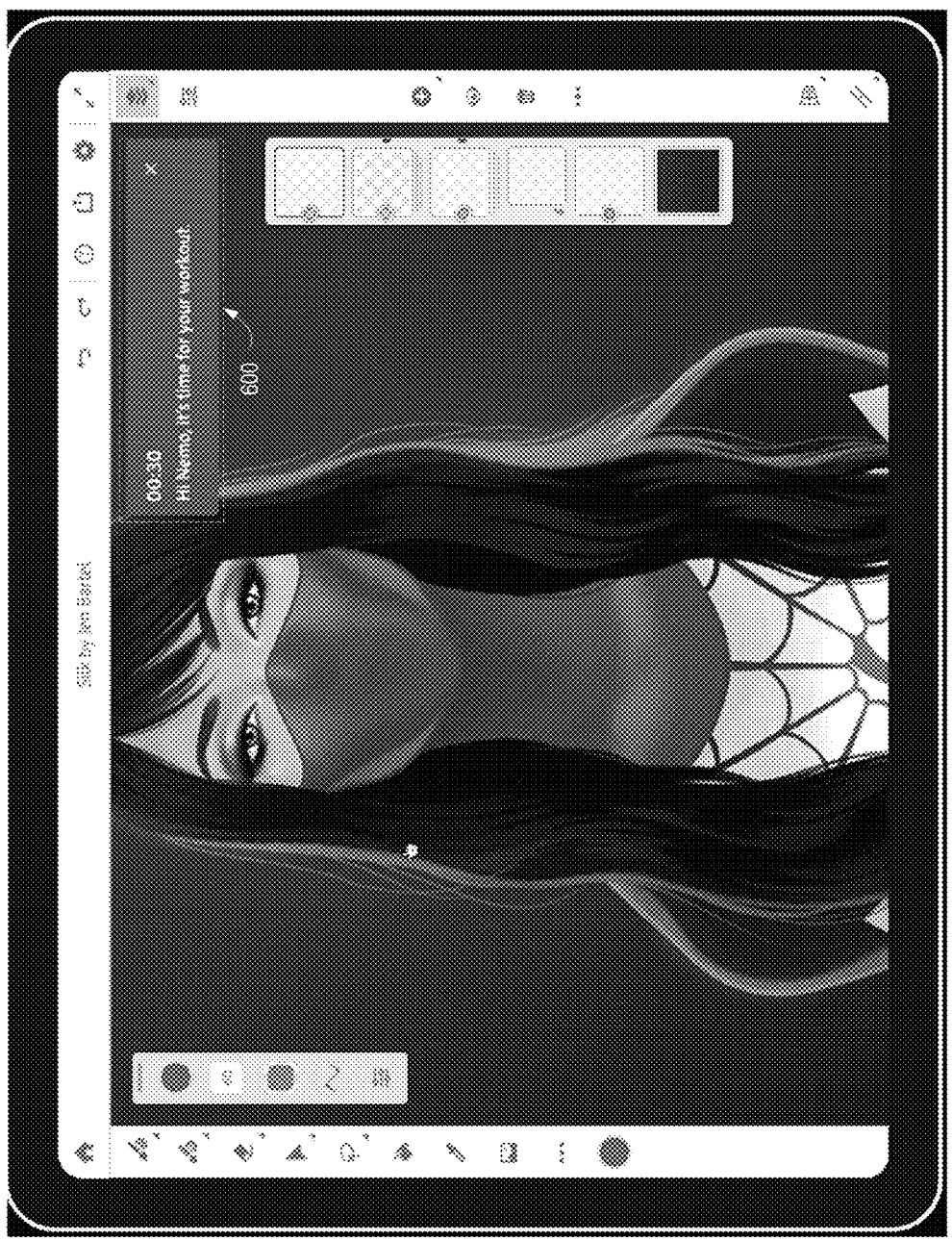
FIG. 6 illustrates an example recommendation notification of a digital design system in accordance with one or more embodiments.

FIG. 6 illustrates an example recommendation notification of a digital design system in accordance with one or more embodiments. As illustrated in FIG. 6, a notification message overlay 600 has been displayed as an overlay on the digital design application. In one or more embodiments, after a set time duration has elapsed, a reminder in the form of a notification message on a notification message overlay 600 can be presented on the user device to remind the user that recommended workouts or actions will be presented shortly. For example, in response to enabling the posture check interface element 304 in FIG. 3, the notification message overlay 600 can periodically display a message recommending the user check their posture. In one or more embodiments, the workout or action recommendation is generated based on the user's interactions with the digital design application. In one or more embodiments, the duration after which workout or action recommendations are shown is a hybrid dependent on the strain being put on a particular body part as well the duration set by the user. If a user mixes the type of strokes they are performing with the digital design system, they may not be straining one body part extensively and the digital design system may generate a workout or action recommendation after a time limit between breaks has elapsed. However, if the user is repeatedly performing the same action, the digital design system may generate a workout or action recommendation which tries to relieve that body part. For example, a couple hundred short strokes can induce a wrist workout and rest recommendation, independent of whether the set time limit has reached.

In one or more embodiments, during periods where a user is waiting for a particular action to complete before proceeding further (e.g., syncing documents between different apps or platforms), the waiting period can be utilized by the digital design system to recommend a workout or action (e.g., suggest the user stand up and perform a quick stretch).

The digital design system can also target workout and action recommendation based on the types of user devices being utilized. For example, working with tablet devices can pose challenges for screen angle and stability, which may not be the case with a desktop or laptop computer.

In one or more embodiments, the user can either select, dismiss, or not interact with the notification message overlay 600. In response to dismissing the notification message in the notification message overlay 600, the notification message is removed. The notification can be associated with a timer and the user can choose to dismiss the notification message overlay 600 (e.g., which can allow the user to avoid the workout), select the notification message overlay 600, or not interact with the notification message overlay 600.

Figure 7:
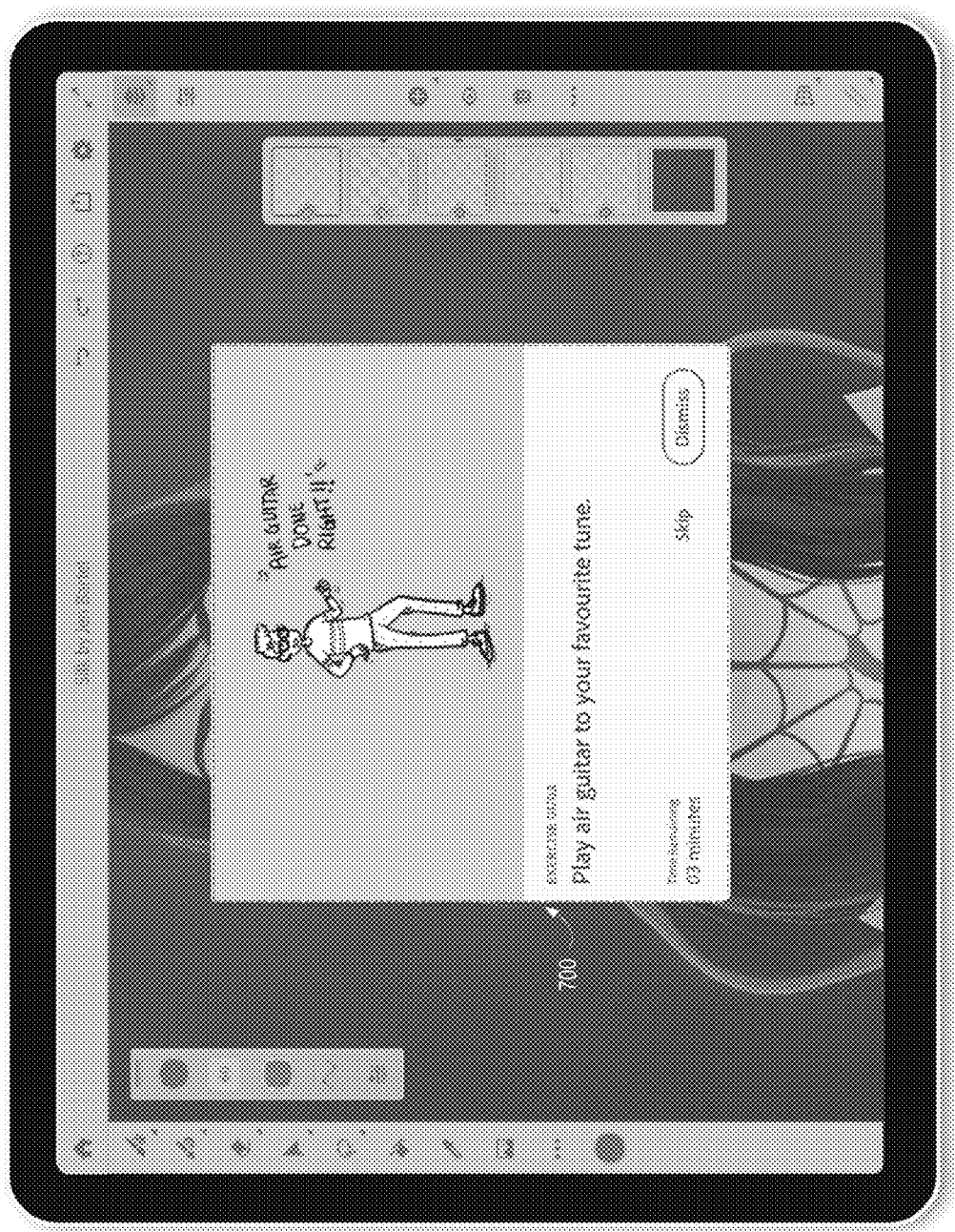
FIG. 7 illustrates an example recommendation interface of a digital design system in accordance with one or more embodiments.

FIG. 7 illustrates an example recommendation interface of a digital design system in accordance with one or more embodiments. Upon selecting the notification message overlay 600, or after a specified amount of time (e.g., 30 seconds) without any user interaction with the notification message overlay 600, a recommendation interface 700 is displayed on the user device 200. The recommendation interface 700 can indicate a workout or action recommended based on the user interactions with the digital design application. In one or more embodiments, the recommendation interface 700 can include multiple workouts or actions. In one or more embodiments, the recommendation interface 700 can present of set of images or animations detailing the recommended workouts and and/or actions.

In one or more embodiments, the workout and/or action recommendations can be selected by an algorithm. The workout and/or action can be curated by the digital design system based on the area of the user impacted by the user's interactions with the digital design system and/or the type of user device being used by the user. For example, stroke data from the digital design system and other applications can be used to determine the type of hand movements being performed, as different types of hand movements can require ergonomic attention to different parts of the body. The hand movements can be categorized as small arc, large arcs, etc., and the information can be used to identify the stress on the respective area of the arm primarily used to support that motion. In another example, long interactions (e.g., based on time) with a document, project, or application can be used to estimate stress points (e.g., eye strain). Further, the workouts/actions selected as "favorites" by the user (e.g., in workouts interface 400 of FIG. 4) can also be used in curating the workouts and/or actions selected for the user.

The recommendation interface 700 can include interface elements to skip a specific recommended workout or action or to dismiss the recommendation entirely and close the recommendation interface 700. In one or more embodiments, in response to the user skipping a particular workout or action recommendation, the digital design system can display a dialog box indicating why the workout or action was relevant and specifically chosen for the user.

Figure 8:
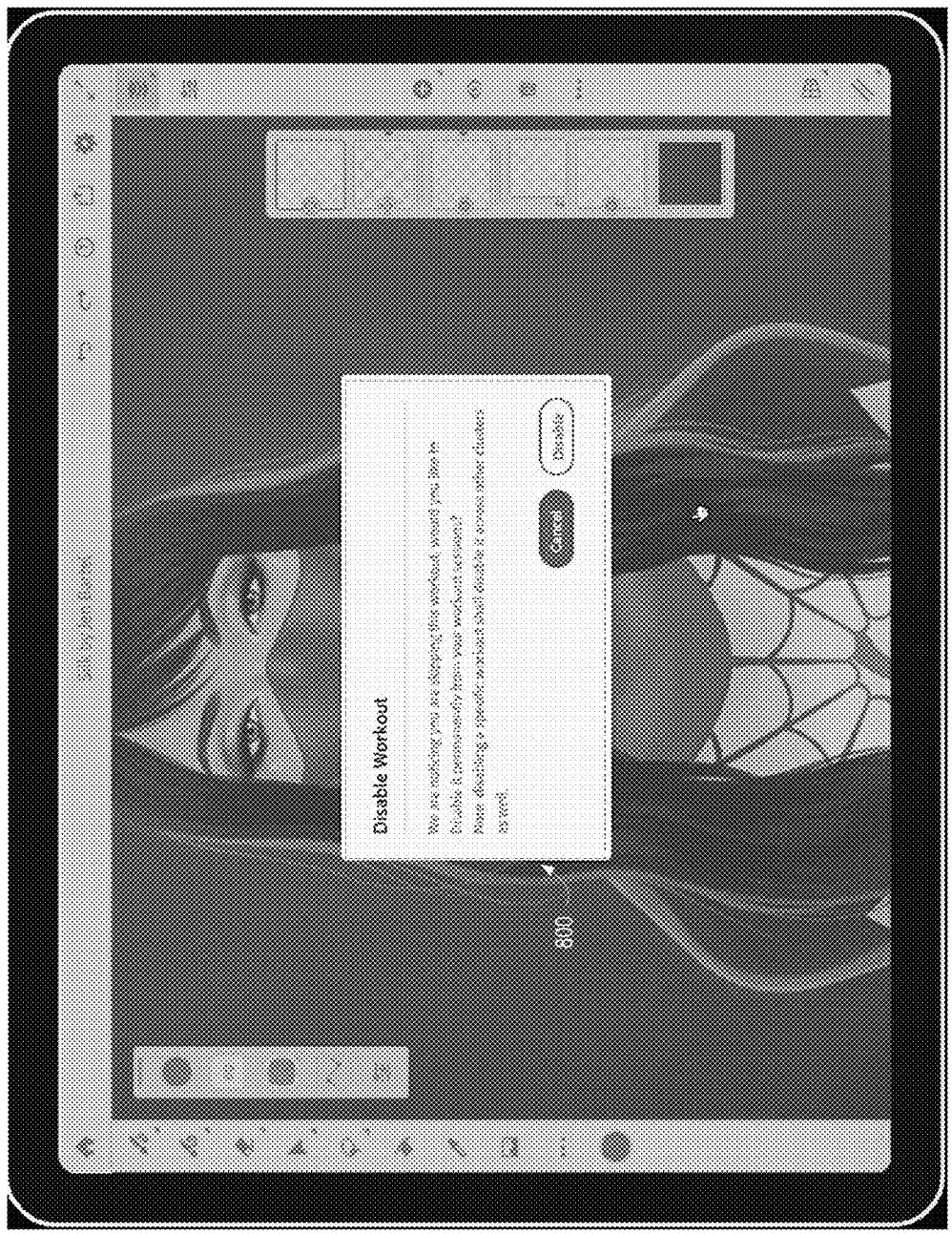
FIG. 8 illustrates an example disable workout interface of a digital design system in accordance with one or more embodiments.

FIG. 8 illustrates an example disable workout interface of a digital design system in accordance with one or more embodiments. In one or more embodiments, when the digital design system identifies that the user has skipped a particular workout or action recommendation more than a threshold number of times, the digital design system can display a dialog box asking the user if they would like to permanently disable the particular workout or action. If the user selects to disable the particular workout or action, the digital design system will remove the particular workout or action from consideration as an option for subsequent recommendations.

Figure 9:
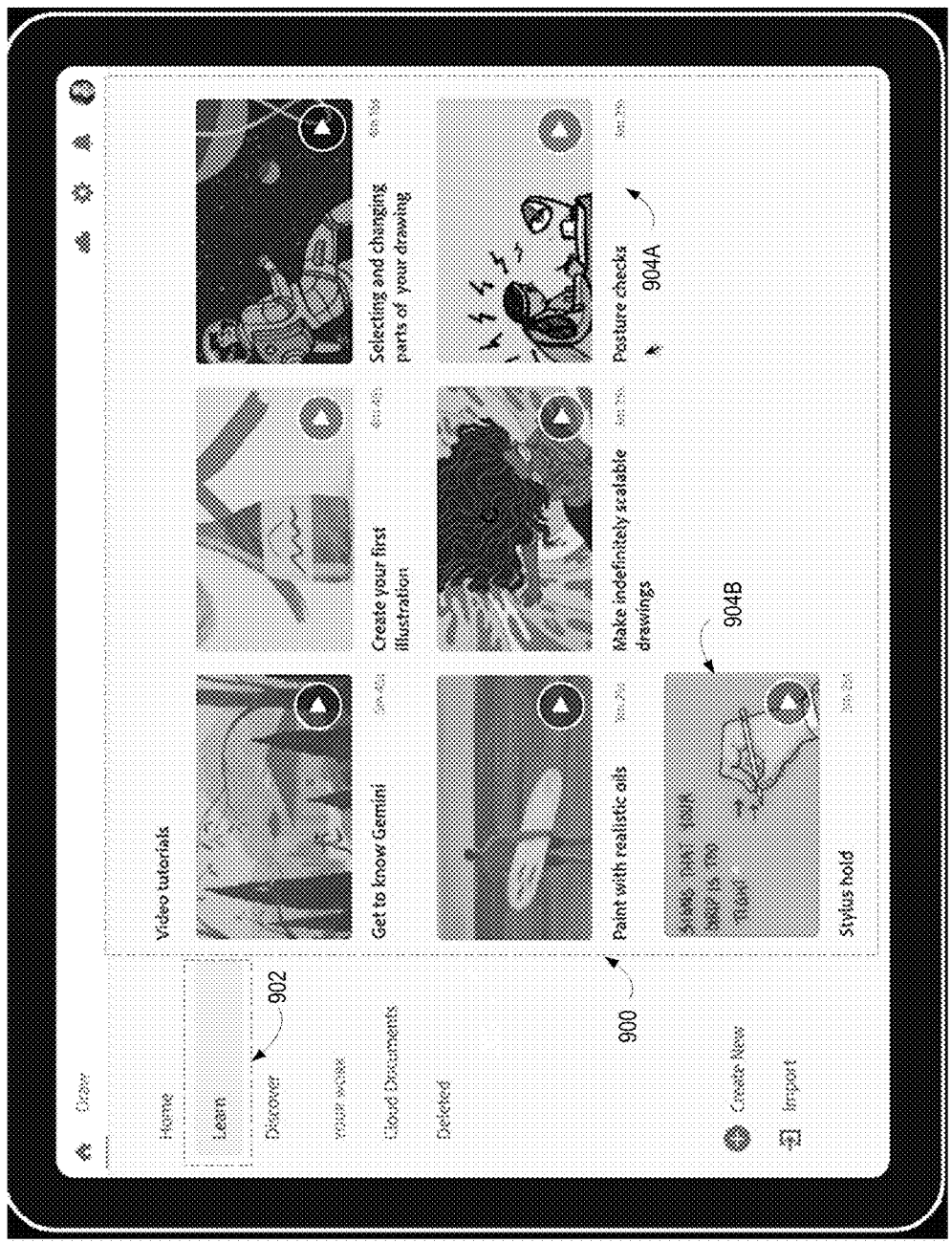
FIG. 9 illustrates an example tutorials interface of a digital design system in accordance with one or more embodiments.

FIG. 9 illustrates an example tutorials interface of a digital design system in accordance with one or more embodiments. As illustrated in FIG. 9, the tutorials interface 900 displays a plurality of multimedia files that can instruct the user regarding various features of the digital design application, including wellness tutorials. For example, a "Learn" interface element 902 in a menu or home screen of the digital design system can be selected to display the tutorials interface 900. The tutorials interface 900 can provide information regarding drawing methods and techniques to users.

As illustrated in FIG. 9, multimedia (e.g., videos, gifs, etc.) in the tutorials interface 900 can include tutorials 904A-B focusing on the needs of wellbeing and can assist users in understanding various issues related to health. Examples include a posture check video explaining how to maintain the correct posture while illustrating and a stylus hold video explaining the proper way to hold a stylus to reduce injury. Other embodiments can include addition wellbeing-related tutorials.

Figure 10:
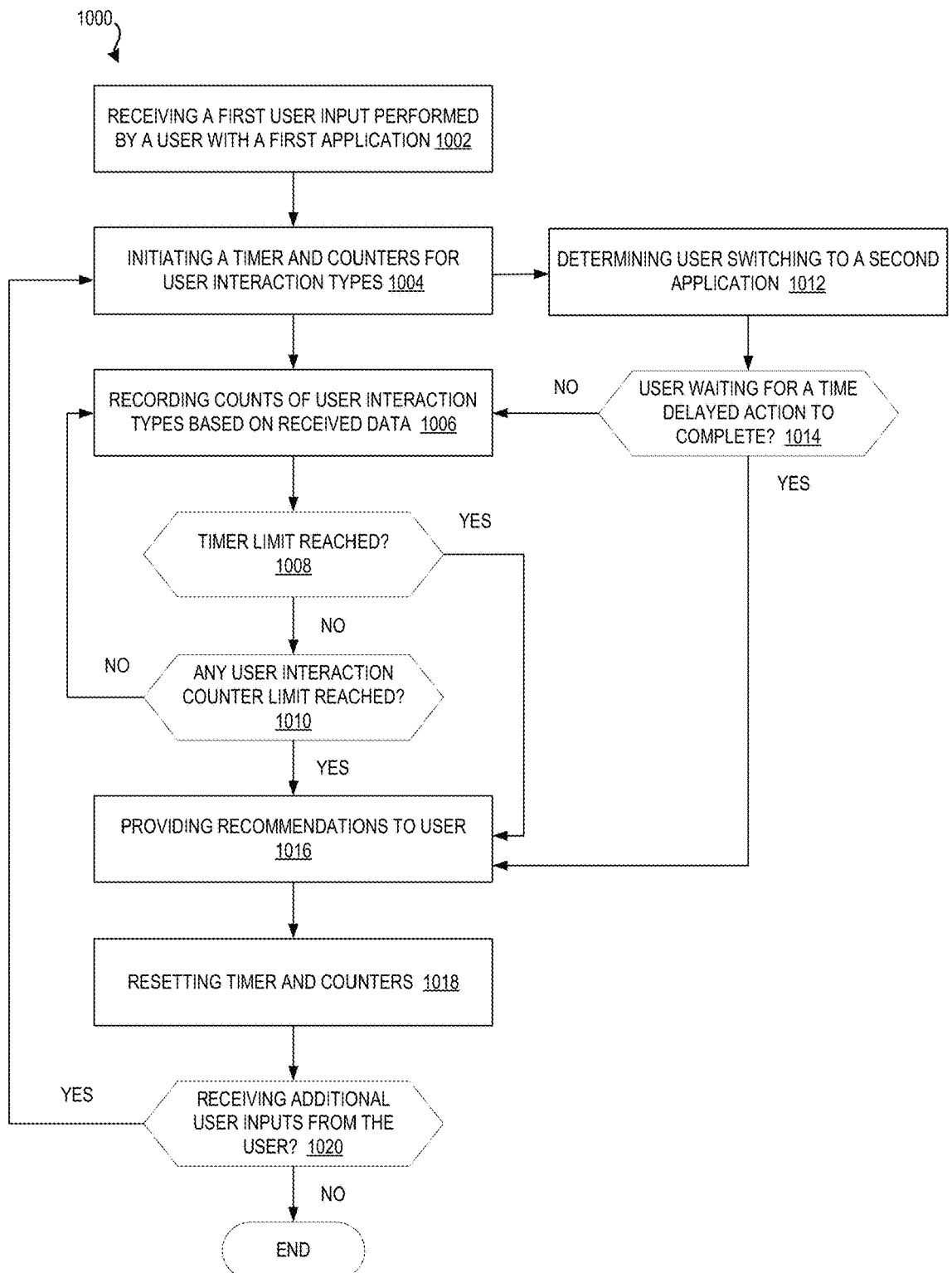
FIG. 10 illustrates a flowchart of a series of acts in a method of monitoring user interactions and providing recommendations in a digital design system in accordance with one or more embodiments.

FIG. 10 illustrates a flowchart of a series of acts in a method of monitoring user interactions and providing recommendations in a digital design system in accordance with one or more embodiments. At 1002, the digital design system receives a first user input performed by a user with a first application. In one or more embodiments, the first user input can be opening a digital design system application, performing a first interaction with the digital design system application, etc.

At 1004, the digital design system initiates a timer to track the amount the time the user is interacting with the digital design system and counters for each of a plurality of user interaction types. In one or more embodiments, initiating the timer and the counters can include resetting the timer and counters to a starting value (e.g., zero).

At 1006, using the counters, the digital design system records the counts of user interaction types based on received user inputs. In one or more embodiments, the digital design system identifies a user interaction type for each user interaction received from a computing device of the user and increments corresponding counters.

At 1008, the digital design system determines whether a timer limit for the timer associated with the user has been reached. When the timer limit has not been reached, the method continues to act 1010. When the timer limit has been reached, the method continues to act 1016.

At 1010, the digital design system determines whether any user interaction type counter limit has been reached. In one or more embodiments, the counter limit can be used on the usage history of the user. When no user interaction type counter limit has been reached, the method returns to act 1006 to continue recording counts of user interaction types based on received data. When a user interaction type counter limit has been reached, the method continues to act 1016.

At 1012, the digital design system determines that the user has switched to performing interactions with a second application. For example, the digital design system can begin receiving user interaction data from a linked application to continue monitoring the user interactions being performed by the user.

At 1014, the digital design system determines whether the user is waiting for a time delayed action to complete. Example time delayed action can include waiting for the second application to sync or a file to download. When the user is waiting for a time delayed action to complete, the method continues to act 1016. When the user is not waiting for a time delayed action to complete, the method continues to 1006 to record the counts of user interactions based on received data from the second application.

At 1016, the digital design system provides workout/action recommendations to the user. In one or more embodiments, the digital design system queries a database for recommended workouts and/or actions for mitigating negative effects from a user interaction type that has reached a counter limit or from extended usage of or interactions with the digital design system (e.g., based on reaching the timer limit). The digital design system can also retrieve workouts and/or actions to recommend to the users while the user is waiting for a time delayed action to complete. The recommendation can be sent in a notification message that includes information associated with the recommended workouts and/or actions. The information associated with the recommended workouts and/or actions can include instructions, diagrams, etc.

At 1018, the digital design system resets the timer and the counters. In one or more embodiments, after providing the recommendations to the user, the digital design system can reset the timer and the counters. In one or more embodiments, the digital design system resets the timer and the counters in response to receiving an indication that the user has performed the workout and/or action in the recommendation.

At 1020, the digital design system determines whether the user is continuing to provide user inputs (e.g., provide user interactions) from the user. In one or more embodiments, the digital design system waits a specified amount of time (e.g., ten minutes) for a user input/interaction before determining whether to continue monitoring user interactions. A shorter break may be an indication of the user switching applications or interacting with other tools, and thus may not require resetting of the time and counters. When the digital design system receives additional user inputs from the user, the method proceeds to act 1004 and the time measured by the timer and the counts of user interaction types are reestablished. When the digital design system does not receive additional user inputs after the specified amount of time (e.g., ten minutes), the process ends.

Figure 11:
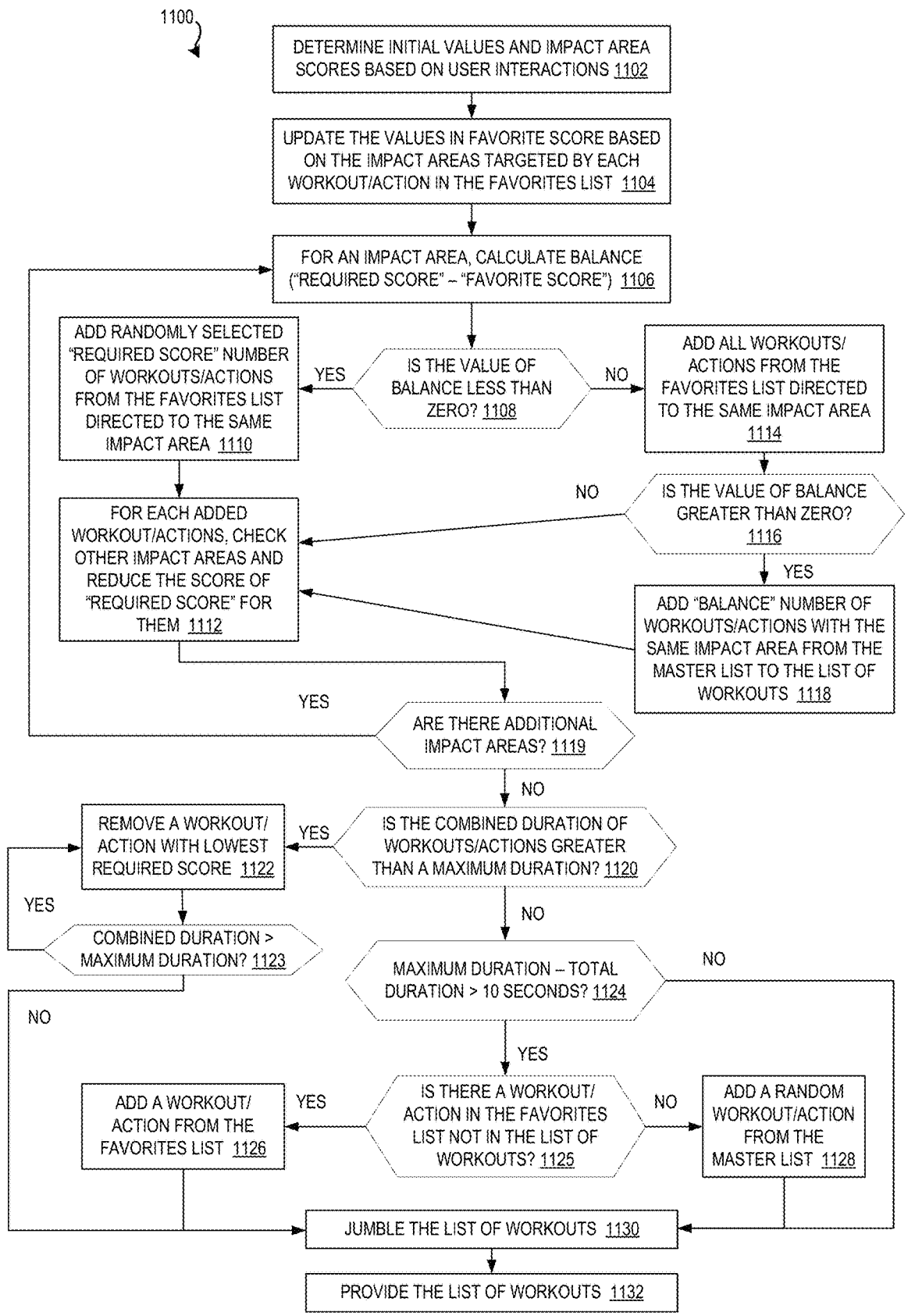
FIG. 11 illustrates a flowchart of a series of acts in a method of determining workout recommendations in a digital design system in accordance with one or more embodiments.

FIG. 11 illustrates a flowchart of a series of acts in a method of determining workout recommendations in a digital design system in accordance with one or more embodiments. In one or more embodiments, the digital design system includes a list of workouts and/or actions stored in a database, where each of the workouts and/or actions can be specified as being directed to one or more impact areas (e.g., wrist, shoulder, back, neck, etc.). In addition, a user can indicate one or more workouts and/or actions as being "favorites," e.g., in a favorites list, as shown in FIG. 4. For example, the user can define "Favorite Workout 1" that has impact areas scores of "Back=2" and "Neck=1," with a duration of two minutes. The user can also define "Favorite Workout 2" has a workout/action that has impact areas scores of "Wrist=2," "Arm=2," and "Back=3," with a duration of one minute. The digital design system can also include additional workouts/action that were not selected as favorites, including "Master List Workout 1", that has an impact areas score of "Wrist=1," with a duration of two minutes, and "Master List Workout 2", that has impact areas scores of "Wrist=1" and "Eye=2," with a duration of two minutes The user can also set a value for "total duration," which is an amount of time the user has established for performing recommended workouts and/or actions per session. For example, a user may define the value for "total duration" as five minutes per session.

At 1102, the digital design system determines initial values and impact area scores based on user interactions. "Required Score" is a catalog or data structure storing values for impact areas denoting the severity of each impact area, based on received user interaction data and/or user device data. Continuing the example, after receiving user interactions, the digital design system can have impact area scores for the user ("Required Score" values) as "Back=2," "Wrist=3," and "Eye=2."

At 1104, the digital design system updates the values in "Favorite Score" based on the impact areas targeted by each workout in the favorites list. "Favorite Score" is a catalog or data structure storing values for all impact areas. For example, after a period of time, the digital design system has values of "Back=5," "Wrist=2", and "Eye=0," from the combination of "Favorite Workout 1" and "Favorite Workout 2."

The digital design system then iteratively processes each impact area through 1106-1118. Continuing the example, the digital design system processes the "Back" impact area through 1106-1118, then the "Wrist" impact area, and then the "Eye" impact area.

At 1106, the digital design system calculates a value of balance for each impact area. The value of "balance" is the remaining amount of time that workouts and/or actions can be added to. The value of balance can be calculated as follows:

Balance=("Required Score"–"Favorite Score")

At 1108, the digital design system determines whether the value of the balance is less than zero. When the balance is less than zero, the method proceeds to 1110. When the balance is not less than zero, the method proceeds to 1114.

At 1110, when the value of balance is less than zero, the digital design system determines the value of "Required Score" and adds a randomly selected number of workouts/actions from the favorites list up to the value. The digital design system randomly selects workouts/actions directed to the same impact area to add to the list of workouts. In one or more embodiments, the workout/action from the favorites list with the highest required score is selected for addition to the list of workouts.

At 1112, the digital design system checks, for each added workout/action, other impact areas that added workout/action benefits and reduces the score of "Required Score" for these other impact areas. In one or more embodiments, the digital design system performs this to prevent adding extra workouts/actions for impact areas already covered.

At 1114, when the value of balance is not less than zero, the digital design system adds all workout/actions from the favorites list directed to the same impact area to the list of workouts. At 1116, the digital design system determines if the value of balance is greater than zero after adding all workouts/actions from the list of favorite workouts. When the balance is not greater than zero, the method proceeds to 1112, described above. When the balance is greater than zero, the method proceeds to 1118.

At 1118, when the value of balance is greater than zero, the digital design system adds "balance" number of workouts/actions from the same impact area from the master list to the list of workouts. The method then proceeds to 1112, described above.

For the "Back" impact area, at 1106, the digital design system determines a value of balance of "–3" from the result of "Required Score" minus "Favorite Score" (i.e., 2 minus 5). At 1108, because the value of balance is less than zero, at 1110, the digital design system adds "Favorite Workout 2" to the list of workouts. At 1112, the digital design system modifies the impact area scores in "Required Score" for the user to "Back=–1" (from "Required Score" of Back minus the impact to Back from Favorite Workout 2), "Wrist=1" (from "Required Score" of Wrist minus the impact to Wrist from Favorite Workout 2), and "Eye=2" (from "Required Score" of Eye minus the impact to Eye from Favorite Workout 2).

At 1119, the digital design system determines if there are additional impact areas to consider. When there are additional impact areas, the method returns to 1106.

For example, the digital design system then analyzes the "Wrist" impact area and then the "Eye" impact area. For the "Wrist" impact area at 1106, the digital design system determines a value of balance of "−1" from "Required Score"−"Favorite Score." At 1108, because the value of balance is less than zero, the method proceeds to 1110. At 1110, no change is made to the list of workouts as there are no other favorite workouts directed to the "Wrist" impact area that is not already in the list of workouts. The list of workouts still contains only "Favorite Workout 2." At 1112, since no workouts were added at 1110, no changes are made to the values in "Required Score." The values of "Required Score" remains "Back=−1," "Wrist=1," and "Eye=2"

For the "Eye" impact area, at 1106, the digital design system determines a value of balance of "2" from "Required Score"−"Favorite Score." As the value of balance is not less than zero, the method proceeds to 1114. At 1114, no changes are made to the list of workouts because there are no additional favorite workouts directed to the "Eye" impact area. The list of workouts still contains only "Favorite Workout 2." At 1116, as the value of balance is still "2" and thus not less than zero, the method proceeds to 1118. At 1118, the digital design system adds "Master List Workout 2" to the list of workouts as it is directed to the "Eye" impact area. The list of workouts now contains "Favorite Workout 2" and "Master List Workout 1." The method then proceeds to 1112, where the values in "Required Score" are changed to "Back=−1," "Wrist=0," and "Eye=0."

At 1119, when there are no additional impact areas to consider, the method proceeds to 1120.

At 1120, the digital design system determines if the combined duration of workouts/actions is greater than a maximum duration (e.g., the user-defined "total duration"). When the combined duration is greater than the maximum duration, the method proceeds to 1122. When the combined duration is not greater than the maximum duration, the method proceeds to 1124.

Continuing the example, the combined duration of "Favorite Workout 2" and "Master List Workout 1" is three minutes. In this example, as the combined duration (i.e., three minutes) is less than the maximum duration (i.e., five minutes), the example would proceed to 1124.

At 1122, the digital design system removes a workout/action from the list of workouts. In one or more embodiments, the workout/action with the lowest Required Score is removed. In one or more embodiments, when there is a tie, the digital design system can remove the workout/action affecting the fewest number of impact areas. At 1123, the digital design system determines whether the combined duration is still greater than the maximum duration. When the combined duration is still greater than the maximum duration, the digital design system returns to 1122 and can iteratively remove workouts/actions until the combined duration is no longer greater than the maximum duration. When the combined duration is not greater than the maximum duration, the method proceeds to 1130.

At 1124, the digital design system determines if the difference between the total durations of workouts/actions and the maximum duration is greater than ten seconds (e.g., maximum duration is greater than total duration by more than ten seconds). When the difference is greater than ten seconds, the method proceeds to 1125. When the difference is not greater than ten seconds, the method proceeds to 1130.

At 1125, the digital design system determines whether there is a workout/action in the favorites list that has not already been added to the list of workouts. When there is a workout/action in the favorites list that has not already been added to the list of workouts, the method proceeds to 1126. When there is not a workout/action in the favorites list that has not already been added to the list of workouts, the method proceeds to 1128.

At 1126, the digital design system adds a workout/action from the favorites list to the list of workouts until the difference between the combined duration and the maximum duration is less than ten seconds. In one or more embodiments, the digital design system can iteratively add workouts/actions from the favorites list while the difference between the combined duration and the maximum duration is greater than ten seconds and there are still workouts/actions in the favorites list not in the list of workouts.

The method then proceeds to 1130. In one or more embodiments, if there is still additional time available after adding all the workouts/actions from the favorites list, additional workouts/actions can be added from the master list.

Continuing the example, because the combined duration is less than the maximum duration, and is greater than ten seconds, at 1126, the digital design system adds "Favorite Workout 1" to the list of workouts. The list of workouts now contains "Favorite Workout 2," "Master List Workout 1," and "Favorite Workout 1."

At 1128, the digital design system adds a random workout/action from the master list to the list of workouts. In one or more embodiments, the digital design system can iteratively add workouts/actions from the master list while the difference between the combined duration and the maximum duration is greater than ten seconds and there are still workouts/actions in the master list not in the list of workouts. The method then proceeds to act 1130. At 1130, the digital design system jumbles or randomizes the list of workouts/actions. For example, the order of "Favorite Workout 2," "Master List Workout 1," and "Favorite Workout 1" is randomized. At 1132, the digital design system provides the list of workouts/actions as output. For example, the list of workouts/actions can be provided via a notification message to the user.

Figure 12:
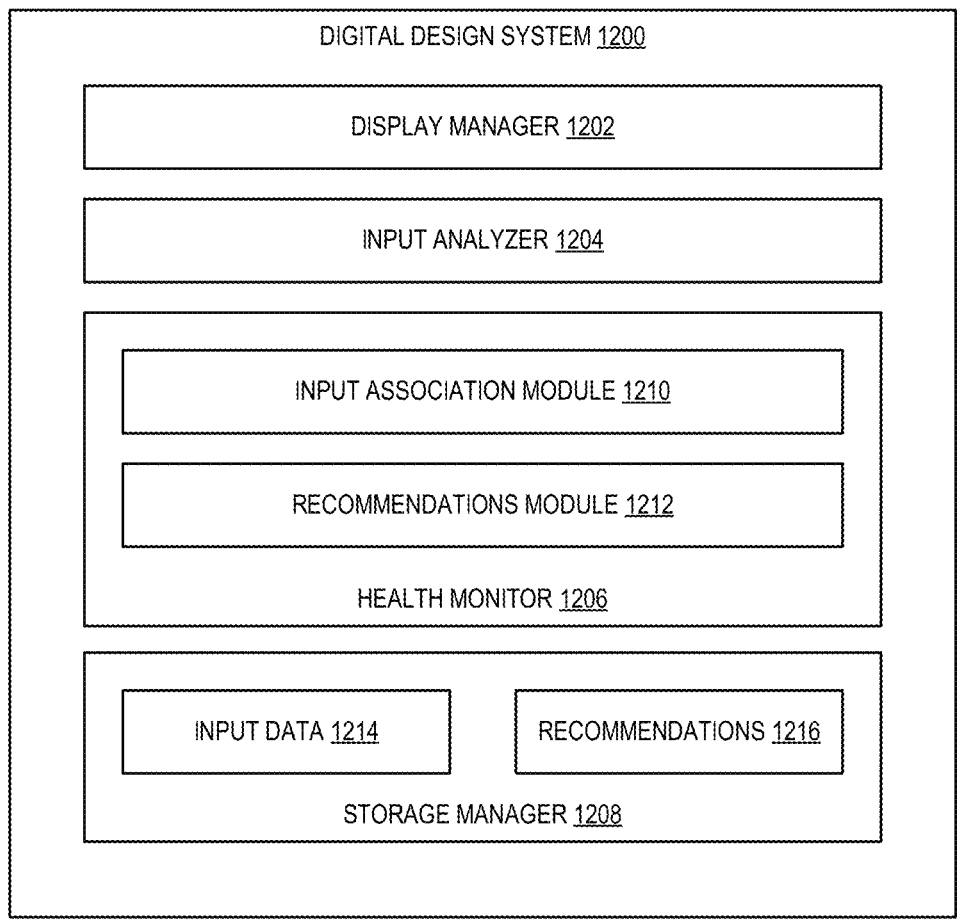
FIG. 12 illustrates a schematic diagram of a digital design system in accordance with one or more embodiments.

FIG. 12 illustrates a schematic diagram of a digital design system (e.g., "digital design system" described above) in accordance with one or more embodiments. As shown, the digital design system 1200 may include, but is not limited to, a display manager 1202, an input analyzer 1204, a health monitor 1206, and a storage manager 1208. As shown, the health monitor 1206 includes an input association module 1210 and a recommendations module 1212. The storage manager 1208 includes input data database 1214 and recommendations database 1216.

As illustrated in FIG. 12, the digital design system 1200 includes a display manager 1202. In one or more embodiments, the display manager 1202 identifies, provides, manages, and/or controls a user interface provided on a touch screen or other device. Examples of displays include interactive whiteboards, graphical user interfaces (or simply "user interfaces") that allow a user to view and interact with content items, or other items capable of display on a touch screen. For example, the display manager 1202 may identify, display, update, or otherwise provide various user interfaces that include one or more display elements in various layouts. In one or more embodiments, the display manager 1202 can identify a display provided on a touch screen or other types of displays (e.g., including monitors, projectors, headsets, etc.) that may be interacted with using a variety of input devices. For example, a display may include a graphical user interface including one or more display elements capable of being interacted with via one or more touch gestures or other types of user inputs (e.g., using a stylus, a mouse, or other input devices). Display elements include, but are not limited to buttons, text boxes, menus, thumbnails, scroll bars, hyperlinks, etc.

As further illustrated in FIG. 12, the digital design system 1200 also includes an input analyzer 1204. The input analyzer 1204 analyzes an input received by the digital design system 1200 to identify one or more of user interaction data, device data, etc. The user interaction data can include keystroke data, stylus data, touch screen interaction data, etc. The user interaction data can include discrete user interactions (e.g., a user tap on a touch screen) and/or a series of user interactions performed over a period of time (e.g., a series of user strokes performed using one or more input devices). The device data can include information indicating a type of user device (e.g., tablet, mobile device, laptop computer, desktop computer, etc.) being used by the user to interact with the digital design system 1200.

As further illustrated in FIG. 12, the digital design system 1200 also includes a health monitor 1206. In one or more embodiments, the health monitor 1206 includes an input association module 1210 configured to categorize user interaction data received by the health monitor 1206 into one of a plurality of user interaction types. In one or more embodiments, as the input association module 1210 categorizes user interactions, the input association module 1210 increments counters corresponding to the user interaction type detected.

As further illustrated in FIG. 12, the health monitor 1206 includes a recommendations module 1212 configured to query a recommendations data database 1216 for workouts and/or actions to recommend based on received user interaction data. The recommendations module 1212 is further configured to generate a notification message that can be displayed (e.g., as an overlay) on a user device executing the digital design system 1200.

As further illustrated in FIG. 12, the storage manager 1208 includes input data database 1214 and recommendations database 1216. In particular, the input data database 1214 may include input data received by the digital design system 1200 from a user, including user interaction data, device data, etc. The recommendations database 1216 may include the data of workouts and/or actions that can be recommended to users. In one or more embodiments, the workouts and/or actions data in recommendations database 1216 can be associated with identifiers for specific parts of the body that the workouts and/or actions are directed to. For example, workouts and/or actions directed to mitigating injury to a user's wrist can be assigned a first identifier, while workouts and/or actions directed to mitigating neck strain can be assigned a second identifier, and so on. When the health monitor 1206 queries the recommendations database 1216, recommended workouts and/or actions can then be returned based on the query.

Each of the components 1202-1108 of the digital design system 1200 and their corresponding elements (as shown in FIG. 12) may be in communication with one another using any suitable communication technologies. It will be recognized that although components 1202-1108 and their corresponding elements are shown to be separate in FIG. 12, any of components 1202-1108 and their corresponding elements may be combined into fewer components, such as into a single facility or module, divided into more components, or configured into different components as may serve a particular embodiment.

The components 1202-1108 and their corresponding elements can comprise software, hardware, or both. For example, the components 1202-1108 and their corresponding elements can comprise one or more instructions stored on a computer-readable storage medium and executable by processors of one or more computing devices. When executed by the one or more processors, the computer-executable instructions of the digital design system 1200 can cause a client device and/or a server device to perform the methods described herein. Alternatively, the components 1202-1108 and their corresponding elements can comprise hardware, such as a special purpose processing device to perform a certain function or group of functions. Additionally, the components 1202-1108 and their corresponding elements can comprise a combination of computer-executable instructions and hardware.

Furthermore, the components 1202-1108 of the digital design system 1200 may, for example, be implemented as one or more stand-alone applications, as one or more modules of an application, as one or more plug-ins, as one or more library functions or functions that may be called by other applications, and/or as a cloud-computing model. Thus, the components 1202-1108 of the digital design system 1200 may be implemented as a stand-alone application, such as a desktop or mobile application. Furthermore, the components 1202-1108 of the digital design system 1200 may be implemented as one or more web-based applications hosted on a remote server. Alternatively, or additionally, the components of the digital design system 1200 may be implemented in a suit of mobile device applications or "apps." To illustrate, the components of the digital design system 1200 may be implemented in a document processing application or an image processing application, including but not limited to ADOBE® PHOTOSHOP®, ADOBE® FRESCO®, ADOBE® PREMIERE® PRO, etc., or a cloud-based suite of applications such as CREATIVE CLOUD®. "ADOBE®," "PHOTOSHOP®," "ADOBE PREMIERE®," and "CREATIVE CLOUD®" are either a registered trademark or trademark of Adobe Inc. in the United States and/or other countries.

Figure 13:
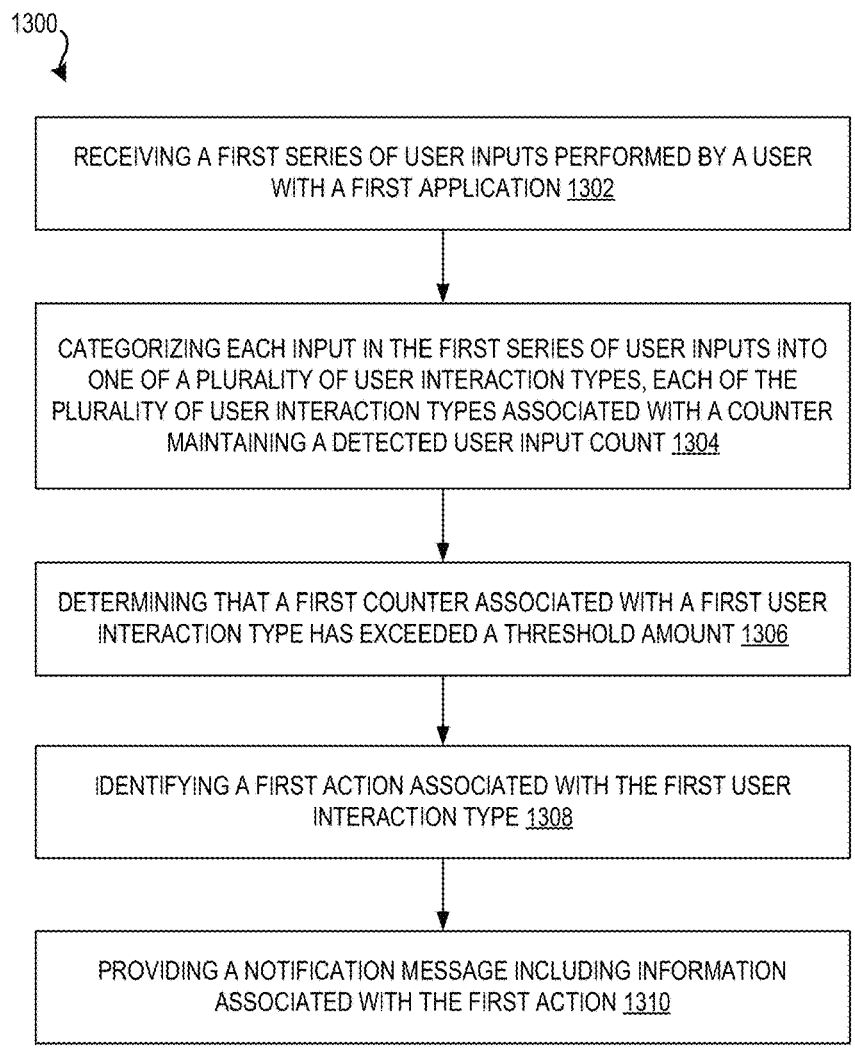
FIG. 13 illustrates a flowchart of a series of acts in a method of providing recommendations based on monitored user inputs in accordance with one or more embodiments.

FIGS. 1-11, the corresponding text, and the examples, provide a number of different systems and devices that allow a digital design system to provide recommendations based on monitored user inputs. In addition to the foregoing, embodiments can also be described in terms of flowcharts comprising acts and steps in a method for accomplishing a particular result. For example, FIG. 13 illustrates a flowchart of an exemplary method in accordance with one or more embodiments. The method described in relation to FIG. 13 may be performed with less or more steps/acts or the steps/acts may be performed in differing orders. Additionally, the steps/acts described herein may be repeated or performed in parallel with one another or in parallel with different instances of the same or similar steps/acts.

FIG. 13 illustrates a flowchart of a series of acts in a method of providing recommendations based on monitored user inputs in accordance with one or more embodiments. In one or more embodiments, the method 1300 is performed in a digital medium environment that includes the digital design system 1200. The method 1300 is intended to be illustrative of one or more methods in accordance with the present disclosure and is not intended to limit potential embodiments. Alternative embodiments can include additional, fewer, or different steps than those articulated in FIG. 13.

As shown in FIG. 13, the method 1300 includes an act 1302 of receiving a first series of user inputs performed by a user with a first application. In one or more embodiments, the digital design system receives the first series of user inputs from a user (e.g., via a computing device). The first series of user inputs can include user interactions performed with the digital design system. Examples of user interactions can include keystroke data, stylus data, touch screen interaction data, etc. The user interaction data can include discrete user interactions (e.g., a user tap on a touch screen) and/or a series of user interactions performed over a period of time (e.g., a series of short and/or long user strokes performed using one or more input devices).

In one or more embodiments, in addition to the first series of user inputs, the digital design system also receives user device data, e.g., a user device type. In such embodiments, the digital design system further determines a set of user interaction types to be tracked based on the user device data. For example, a first set of user interaction types to be tracked may be associated with a mobile device or smartphone, while a second set of user interaction types to be tracked may be associated with a desktop computer, where one or more user interaction types may be associated with both the first and second sets.

As shown in FIG. 13, the method 1300 also includes an act 1304 of categorizing each input in the first series of user inputs into one of a plurality of user interaction types, where each of the plurality of user interaction types is associated with a counter maintaining a detected user input count. In one or more embodiments, the digital design system analyzes the first series of user inputs to determine the type(s) of user interactions being performed. The digital design system increments a counter associated with a user interaction type in response to determining that a user interaction of the corresponding user interaction type has occurred.

In one or more embodiments, the digital design system can additionally, or alternatively receive a second series of user inputs performed by the user with a second application. In such embodiments, the digital design system can increment a counter for a first user interaction type in response to receiving inputs indicating the first user interaction type from either the first application or the second application.

As shown in FIG. 13, the method 1300 also includes an act 1306 of determining that a first counter associated with a first user interaction type has exceeded a threshold amount. In one or more embodiments, the threshold amount for each user interaction type can vary based on the type of user interaction and its expected or estimated effects on a user's health.

As shown in FIG. 13, the method 1300 also includes an act 1308 of identifying a first action associated with the first user interaction type. In one or more embodiments, the digital design system accesses or queries a recommendations database to retrieve one or more workouts and/or actions that can mitigate the harmful effects of performing certain user interaction types. For example, quick short strokes can lead to wrist strain, while long arcing strokes can lead to shoulder strain, and mitigating the effects of each user interaction type may be based on performing different workouts and/or actions.

As shown in FIG. 13, the method 1300 also includes an act 1310 of providing a notification message including information associated with the first action. For example, the notification message can be rendered on a display of a user computing device, stored in a memory or storage location, etc. In one or more embodiments, after providing the notification message, the digital design system can reset a counter associated with the first interaction type.

In one or more embodiments, the digital design system further receives a user response to the notification message. For example, the user response can indicate that the has performed the recommended first action or that the user has provided an input to skip or dismiss the recommendation. In response to the user response, the digital design system can modify a list of workout and/or actions. For example, where the digital design system, determines that the user response to the notification message is an indication to skip the notification message (e.g., not perform the first action), the digital design system increments a second counter associated with the first action. The second counter can represent an interest level of the user with respect to the first action, where the second counter is incremented with each skip response from the user. When the digital design system determines that the value of the second counter associated with the first action is above a threshold value, the digital design system removes the first action from the suggested list of actions.

In one or more embodiments, the digital design system can further generate a notification message including a recommended action based on time, regardless of the counters associated with user interaction types. For example, in response to receiving a first user input, the digital design system initiates a timer. In response to the timer exceeding a predetermined amount of time, the digital design system can provide a notification message including information associated with an action to perform.

In another example, where the digital design system determines that a time delayed action is being performed, the digital design system can provide a notification to the user including information associated with an action to perform while the time delayed action is being performed. In one example, the digital design system provides a recommendation to the user to stand up and stretch while documents are being synced between applications or platforms or while a rendering process is being performed.

Figure 14:
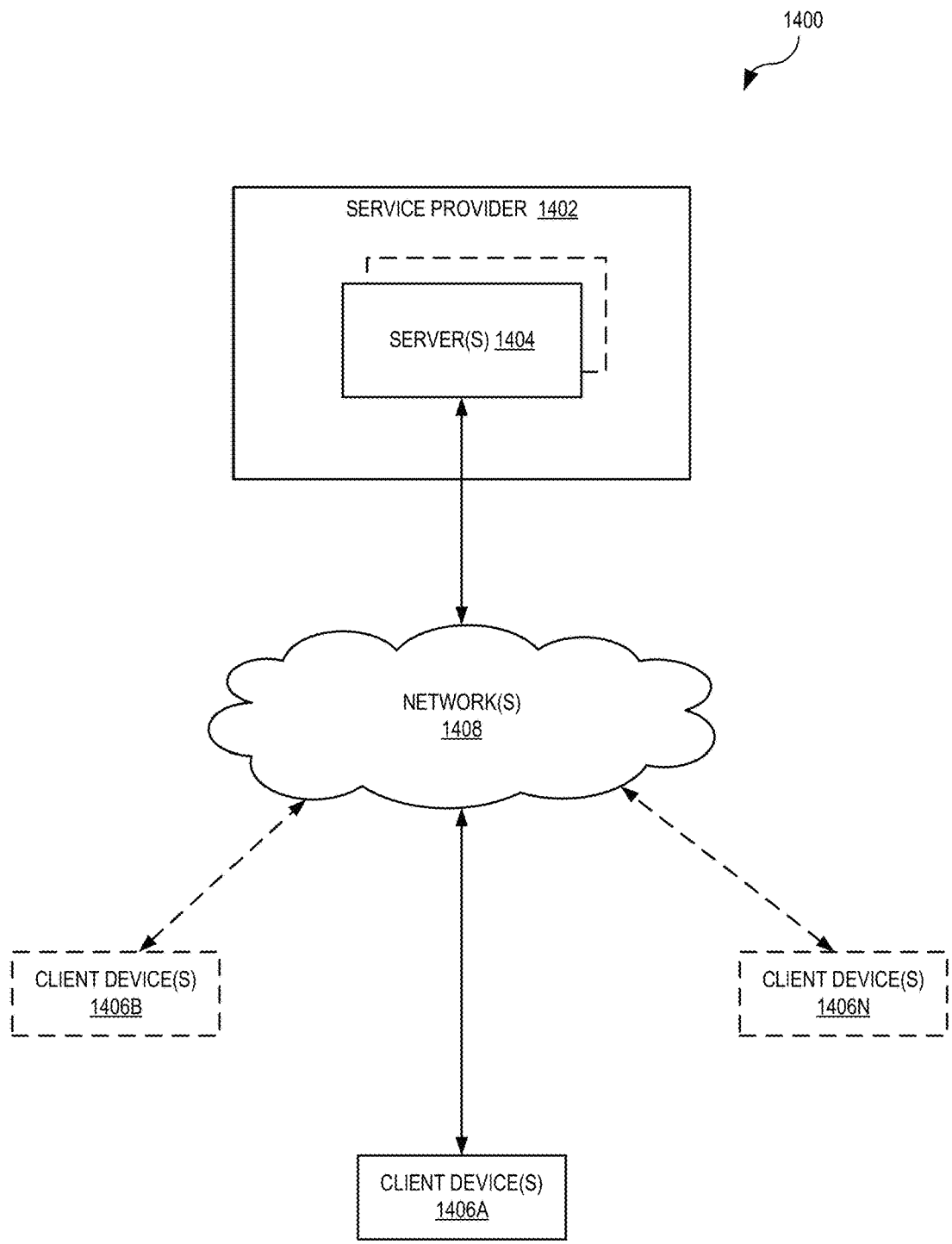
FIG. 14 illustrates a schematic diagram of an exemplary environment in which the digital design system can operate in accordance with one or more embodiments.

FIG. 14 illustrates a schematic diagram of an exemplary environment 1400 in which the digital design system 1200 can operate in accordance with one or more embodiments. In one or more embodiments, the environment 1400 includes a service provider 1402 which may include one or more servers 1404 connected to a plurality of client devices 1406A-1406N via one or more networks 1408. The client devices 1406A-1406N, the one or more networks 1408, the service provider 1402, and the one or more servers 1404 may communicate with each other or other components using any communication platforms and technologies suitable for transporting data and/or communication signals, including any known communication technologies, devices, media, and protocols supportive of remote data communications, examples of which will be described in more detail below with respect to FIG. 15.

Although FIG. 14 illustrates a particular arrangement of the client devices 1406A-1406N, the one or more networks 1408, the service provider 1402, and the one or more servers 1404, various additional arrangements are possible. For example, the client devices 1406A-1406N may directly communicate with the one or more servers 1404, bypassing the network 1408. Or alternatively, the client devices 1406A-1406N may directly communicate with each other. The service provider 1402 may be a public cloud service provider which owns and operates their own infrastructure in one or more data centers and provides this infrastructure to customers and end users on demand to host applications on the one or more servers 1404. The servers may include one or more hardware servers (e.g., hosts), each with its own computing resources (e.g., processors, memory, disk space, networking bandwidth, etc.) which may be securely divided between multiple customers, each of which may host their own applications on the one or more servers 1404. In some embodiments, the service provider may be a private cloud provider which maintains cloud infrastructure for a single organization. The one or more servers 1404 may similarly include one or more hardware servers, each with its own computing resources, which are divided among applications hosted by the one or more servers for use by members of the organization or their customers.

Similarly, although the environment 1400 of FIG. 14 is depicted as having various components, the environment 1400 may have additional or alternative components. For example, the environment 1400 can be implemented on a single computing device with the digital design system 1200. In particular, the digital design system 1200 may be implemented in whole or in part on the client device 1406A. Alternatively, in some embodiments, the environment 1400 is implemented in a distributed architecture across multiple computing devices.

As illustrated in FIG. 14, the environment 1400 may include client devices 1406A-1406N. The client devices 1406A-1406N may comprise any computing device. For example, client devices 1406A-1406N may comprise one or more personal computers, laptop computers, mobile devices, mobile phones, tablets, special purpose computers, TVs, or other computing devices, including computing devices described below with regard to FIG. 15. Although three client devices are shown in FIG. 14, it will be appreciated that client devices 1406A-1406N may comprise any number of client devices (greater or smaller than shown).

Moreover, as illustrated in FIG. 14, the client devices 1406A-1406N and the one or more servers 1404 may communicate via one or more networks 1408. The one or more networks 1408 may represent a single network or a collection of networks (such as the Internet, a corporate intranet, a virtual private network (VPN), a local area network (LAN), a wireless local network (WLAN), a cellular network, a wide area network (WAN), a metropolitan area network (MAN), or a combination of two or more such networks. Thus, the one or more networks 1408 may be any suitable network over which the client devices 1406A-1406N may access the service provider 1402 and server 1404, or vice versa. The one or more networks 1408 will be discussed in more detail below with regard to FIG. 15.

In addition, the environment 1400 may also include one or more servers 1404. The one or more servers 1404 may generate, store, receive, and transmit any type of data, including input data or other information. For example, a server 1404 may receive data from a client device, such as the client device 1406A, and send the data to another client device, such as the client device 1406B and/or 1406N. The server 1404 can also transmit electronic messages between one or more users of the environment 1400. In one example embodiments, the server 1404 is a data server. The server 1404 can also comprise a communication server or a web-hosting server. Additional details regarding the server 1404 will be discussed below with respect to FIG. 15.

As mentioned, in one or more embodiments, the one or more servers 1404 can include or implement at least a portion of the digital design system 1200. In particular, the digital design system 1200 can comprise an application running on the one or more servers 1404 or a portion of the digital design system 1200 can be downloaded from the one or more servers 1404. For example, the digital design system 1200 can include a web hosting application that allows the client devices 1406A-1406N to interact with content hosted at the one or more servers 1404. To illustrate, in one or more embodiments of the environment 1400, one or more client devices 1406A-1406N can access a webpage supported by the one or more servers 1404. In particular, the client device 1406A can run a web application (e.g., a web browser) to allow a user to access, view, and/or interact with a webpage or website hosted at the one or more servers 1404.

Upon the client device 1406A accessing a webpage or other web application hosted at the one or more servers 1404, in one or more embodiments, the one or more servers 1404 can provide a user of the client device 1406A with an interface to provide inputs, including user settings or configuration data. Upon receiving the user settings or configuration data, the one or more servers 1404 can automatically perform the methods and processes described above to perform providing recommendations based on monitored user inputs in accordance with one or more embodiments.

As just described, the digital design system 1200 may be implemented in whole, or in part, by the individual elements 1402-1408 of the environment 1400. It will be appreciated that although certain components of the digital design system 1200 are described in the previous examples with regard to particular elements of the environment 1400, various alternative implementations are possible. For instance, in one or more embodiments, the digital design system 1200 is implemented on any of the client devices 1406A-1406N. Similarly, in one or more embodiments, the digital design system 1200 may be implemented on the one or more servers 1404. Moreover, different components and functions of the digital design system 1200 may be implemented separately among client devices 1406A-1406N, the one or more servers 1404, and the network 1408.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed at a processor, cause a general-purpose computer, special purpose computer, or special purpose processing device to perform a certain function or group of functions. In some embodiments, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 15:
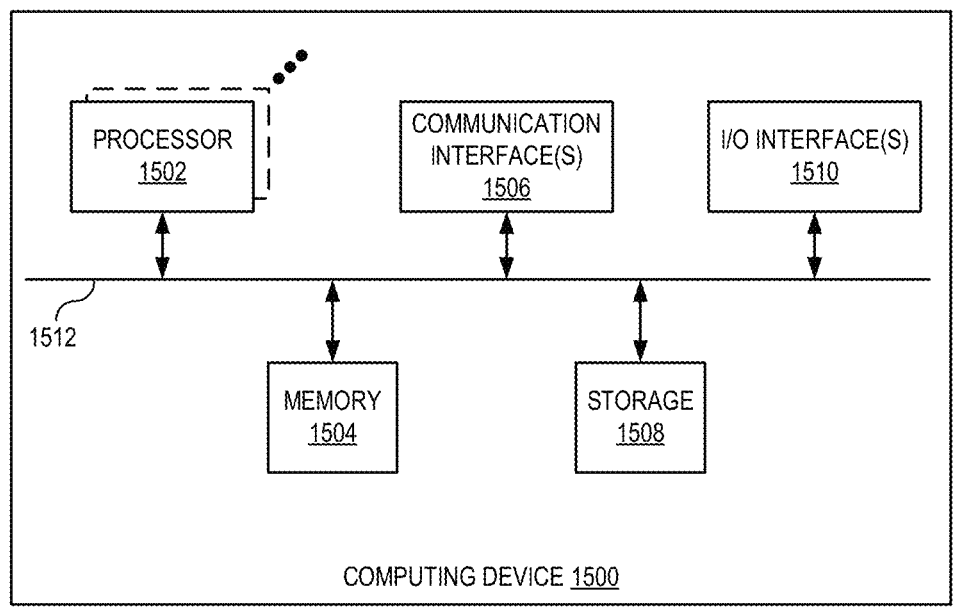
FIG. 15 illustrates a block diagram of an exemplary computing device in accordance with one or more embodiments.

FIG. 15 illustrates, in block diagram form, an exemplary computing device 1500 that may be configured to perform one or more of the processes described above. One will appreciate that one or more computing devices such as the computing device 1500 may implement the digital design system 1200. As shown by FIG. 15, the computing device can comprise a processor 1502, memory 1504, one or more communication interfaces 1506, a storage device 1508, and one or more input or output ("I/O") devices/interfaces 1510. In certain embodiments, the computing device 1500 can include fewer or more components than those shown in FIG. 15. Components of computing device 1500 shown in FIG. 15 will now be described in additional detail.

In particular embodiments, processor(s) 1502 includes hardware for executing instructions, such as those making up a computer program. As an example, and not by way of limitation, to execute instructions, processor(s) 1502 may retrieve (or fetch) the instructions from an internal register, an internal cache, memory 1504, or a storage device 1508 and decode and execute them. In various embodiments, the processor(s) 1502 may include one or more central processing units (CPUs), graphics processing units (GPUs), field programmable gate arrays (FPGAs), systems on chip (SoC), or other processor(s) or combinations of processors.

The computing device 1500 includes memory 1504, which is coupled to the processor(s) 1502. The memory 1504 may be used for storing data, metadata, and programs for execution by the processor(s). The memory 1504 may include one or more of volatile and non-volatile memories, such as Random Access Memory ("RAM"), Read Only Memory ("ROM"), a solid state disk ("SSD"), Flash, Phase Change Memory ("PCM"), or other types of data storage. The memory 1504 may be internal or distributed memory.

The computing device 1500 can further include one or more communication interfaces 1506. A communication interface 1506 can include hardware, software, or both. The communication interface 1506 can provide one or more interfaces for communication (such as, for example, packet-based communication) between the computing device and one or more other computing devices 1500 or one or more networks. As an example, and not by way of limitation, communication interface 1506 may include a network interface controller (NIC) or network adapter for communicating with an Ethernet or other wire-based network or a wireless NIC (WNIC) or wireless adapter for communicating with a wireless network, such as a WI-FI. The computing device 1500 can further include a bus 1512. The bus 1512 can comprise hardware, software, or both that couples components of computing device 1500 to each other.

The computing device 1500 includes a storage device 1508 includes storage for storing data or instructions. As an example, and not by way of limitation, storage device 1508 can comprise a non-transitory storage medium described above. The storage device 1508 may include a hard disk drive (HDD), flash memory, a Universal Serial Bus (USB) drive or a combination these or other storage devices. The computing device 1500 also includes one or more I/O devices/interfaces 1510, which are provided to allow a user to provide input to (such as user strokes), receive output from, and otherwise transfer data to and from the computing device 1500. These I/O devices/interfaces 1510 may include a mouse, keypad or a keyboard, a touch screen, camera, optical scanner, network interface, modem, other known I/O devices or a combination of such I/O devices/interfaces 1510. The touch screen may be activated with a stylus or a finger.

The I/O devices/interfaces 1510 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O devices/interfaces 1510 is configured to provide graphical data to a display for presentation to a user. The graphical data may be representative of one or more graphical user interfaces and/or any other graphical content as may serve a particular implementation.

In the foregoing specification, embodiments have been described with reference to specific exemplary embodiments thereof. Various embodiments are described with reference to details discussed herein, and the accompanying drawings illustrate the various embodiments. The description above and drawings are illustrative of one or more embodiments and are not to be construed as limiting. Numerous specific details are described to provide a thorough understanding of various embodiments.

Embodiments may include other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel with one another or in parallel with different instances of the same or similar steps/acts. The scope of the invention is, therefore, indicated by the appended claims rather than by the foregoing description. All changes that come within the meaning and range of equivalency of the claims are to be embraced within their scope.

In the various embodiments described above, unless specifically noted otherwise, disjunctive language such as the phrase "at least one of A, B, or C," is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

We claim:

1. A computer-implemented method comprising:
   receiving a first series of user inputs performed by a user with a first application;
   categorizing each input in the first series of user inputs into one of a plurality of user interaction types, each of the plurality of user interaction types associated with a counter maintaining a detected user input count;
   determining that a first counter associated with a first user interaction type has exceeded a threshold amount;
   identifying a first action associated with the first user interaction type; and
   providing a notification message including information associated with the first action.

2. The computer-implemented method of claim 1, further comprising:
   receiving user device data, the user device data including a user device type; and
   determining a set of user interaction types to be tracked based on the user device data, each set of user interaction types associated with at least one of the plurality of user interaction types.

3. The computer-implemented method of claim 1, further comprising:
   receiving a first user input;
   in response to receiving the first user input, initiating a timer; and
   in response to the timer exceeding a predetermined amount of time, providing a second notification message including information associated with a second action.

4. The computer-implemented method of claim 1, further comprising:
   determining that the first application is performing a time delayed action; and
   in response to determining that the first application is performing the time delayed action, providing a second notification message including information associated with a second action.

5. The computer-implemented method of claim 1, further comprising:
   receiving a user response to the notification message; and
   modifying a suggested list of actions for the user based on the user response.

6. The computer-implemented method of claim 5, wherein modifying the suggested list of actions for the user based on the user response comprises:
   determining that the user response to the notification message is an indication to skip the notification message;
   incrementing a second counter associated with the first action; and
   determining a value of the second counter associated with the first action is above a threshold value; and removing the first action from the suggested list of actions.

7. The computer-implemented method of claim 1, further comprising:
   receiving a second series of user inputs performed by the user with a second application; and
   in response to determining that first user inputs and second user inputs are of the first user interaction type, incrementing the first counter associated with the first user interaction type based on the first user inputs from the first application and the second user inputs from the second application.

8. The computer-implemented method of claim 1, further comprising:
   in response to providing the notification message including the first action, resetting the first counter associated with the first user interaction type.

9. A non-transitory computer-readable storage medium including instructions stored thereon which, when executed by at least one processor, cause the at least one processor to:

receive a first series of user inputs performed by a user with a first application;
categorize each input in the first series of user inputs into one of a plurality of user interaction types, each of the plurality of user interaction types associated with a counter maintaining a detected user input count;
determine that a first counter associated with a first user interaction type has exceeded a threshold amount;
identify a first action associated with the first user interaction type; and
provide a notification message including information associated with the first action.

10. The non-transitory computer-readable storage medium of claim 9, wherein the instructions, when executed, further cause the at least one processor to:
receive user device data, the user device data including a user device type; and
determine a set of user interaction types to be tracked based on the user device data, each set of user interaction types associated with at least one of the plurality of user interaction types.

11. The non-transitory computer-readable storage medium of claim 9, wherein the instructions, when executed, further cause the at least one processor to:
receive a first user input;
in response to receiving the first user input, initiate a timer; and
in response to the timer exceeding a predetermined amount of time, provide a second notification message including information associated with a second action.

12. The non-transitory computer-readable storage medium of claim 9, wherein the instructions, when executed, further cause the at least one processor to:
receive a user response to the notification message; and
modify a suggested list of actions for the user based on the user response.

13. The non-transitory computer-readable storage medium of claim 12, wherein to modify the suggested list of actions for the user based on the user response, the instructions, when executed, further cause the at least one processor to:
determine that the user response to the notification message is an indication to skip the notification message;
increment a second counter associated with the first action; and
determine a value of the second counter associated with the first action is above a threshold value; and removing the first action from the suggested list of actions.

14. The non-transitory computer-readable storage medium of claim 9, wherein the instructions, when executed, further cause the at least one processor to:
receive a second series of user inputs performed by the user with a second application; and
in response to determining that first user inputs and second user inputs are of the first user interaction type, increment the first counter associated with the first user interaction type based on the first user inputs from the first application and the second user inputs from the second application.

15. A system, comprising:
a computing device including a memory and at least one processor, the computing device implementing a digital design system,
wherein the memory includes instructions stored thereon which, when executed, cause the digital design system to:
receive a first series of user inputs performed by a user with a first application;
categorize each input in the first series of user inputs into one of a plurality of user interaction types, each of the plurality of user interaction types associated with a counter maintaining a detected user input count;
determine that a first counter associated with a first user interaction type has exceeded a threshold amount;
identify a first action associated with the first user interaction type; and
provide a notification message including information associated with the first action.

16. The system of claim 15, wherein the instructions, when executed, further cause the digital design system to:
receive user device data, the user device data including a user device type; and
determine a set of user interaction types to be tracked based on the user device data, each set of user interaction types associated with at least one of the plurality of user interaction types.

17. The system of claim 15, wherein the instructions, when executed, further cause the digital design system to:
receive a first user input;
in response to receiving the first user input, initiate a timer; and
in response to the timer exceeding a predetermined amount of time, provide a second notification message including information associated with a second action.

18. The system of claim 15, wherein the instructions, when executed, further cause the digital design system to:
receive a user response to the notification message; and
modify a suggested list of actions for the user based on the user response.

19. The system of claim 18, wherein the instructions to modify the suggested list of actions for the user based on the user response, further causes the digital design system to:
determine that the user response to the notification message is an indication to skip the notification message;
increment a second counter associated with the first action; and
determine a value of the second counter associated with the first action is above a threshold value; and removing the first action from the suggested list of actions.

20. The system of claim 15, wherein the instructions, when executed, further cause the digital design system to:
receive a second series of user inputs performed by the user with a second application; and
in response to determining that first user inputs and second user inputs are of the first user interaction type, increment the first counter associated with the first user interaction type based on the first user inputs from the first application and the second user inputs from the second application.

* * * * *